United States Patent
Muller et al.

(10) Patent No.: US 9,283,207 B2
(45) Date of Patent: *Mar. 15, 2016

(54) METHODS OF USING (+)-2-[1-(3-ETHOXY-4-METHOXYPHENYL)-2-METHYLSULFONYLETHYL]-4-ACETYLAMINOISOINDOLINE-1,3-DIONE

(71) Applicant: Celgene Corporation, Summit, NJ (US)

(72) Inventors: George W. Muller, Rancho Santa Fe, CA (US); Peter H. Schafer, Belle Mead, NJ (US); Hon-Wah Man, Princeton, NJ (US); Chuansheng Ge, Belle Mead, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/316,160

(22) Filed: Jun. 26, 2014

(65) Prior Publication Data

US 2014/0371287 A1    Dec. 18, 2014

Related U.S. Application Data

(60) Continuation of application No. 13/682,652, filed on Nov. 20, 2012, now Pat. No. 8,802,717, which is a continuation of application No. 12/630,788, filed on Dec. 3, 2009, now Pat. No. 8,455,536, which is a continuation of application No. 12/098,379, filed on Apr. 4, 2008, now Pat. No. 7,659,303, which is a division of application No. 11/170,308, filed on Jun. 28, 2005, now Pat. No. 7,358,272, which is a division of application No. 10/392,195, filed on Mar. 19, 2003, now Pat. No. 6,962,940.

(60) Provisional application No. 60/438,450, filed on Jan. 7, 2003, provisional application No. 60/366,515, filed on Mar. 20, 2002.

(51) Int. Cl.

| A61K 31/4035 | (2006.01) |
|---|---|
| C07D 209/44 | (2006.01) |
| C07C 317/28 | (2006.01) |
| C07D 209/48 | (2006.01) |
| A61K 45/06 | (2006.01) |

(52) U.S. Cl.
CPC ............. *A61K 31/4035* (2013.01); *A61K 45/06* (2013.01); *C07C 317/28* (2013.01); *C07D 209/48* (2013.01); *C07B 2200/07* (2013.01)

(58) Field of Classification Search
CPC .................... A61K 31/4035; C07D 209/44
USPC .................. 548/469, 478; 514/417
See application file for complete search history.

(56) References Cited

U.S. PATENT DOCUMENTS

| 3,031,450 A | 4/1962 | Fischer et al. |
|---|---|---|
| 3,322,755 A | 5/1967 | Roch et al. |
| 3,920,636 A | 11/1975 | Takahashi et al. |
| 4,001,237 A | 1/1977 | Partyka et al. |
| 4,001,238 A | 1/1977 | Partyka et al. |
| 4,047,404 A | 9/1977 | Hayashi |
| 4,060,615 A | 11/1977 | Matier et al. |
| 4,101,548 A | 7/1978 | Crenshaw et al. |
| 4,162,316 A | 7/1979 | Nishimura et al. |
| 4,209,623 A | 6/1980 | Juby |
| 4,880,810 A | 11/1989 | Lowe, III |
| 4,885,301 A | 12/1989 | Coates |
| 5,147,875 A | 9/1992 | Coates et al. |
| 5,354,571 A | 10/1994 | Morikawa et al. |
| 5,401,774 A | 3/1995 | Pamukcu et al. |
| 5,439,895 A | 8/1995 | Lee et al. |
| 5,488,055 A | 1/1996 | Kumar et al. |
| 5,608,914 A | 3/1997 | Keesler |
| 5,614,530 A | 3/1997 | Kumar et al. |
| 5,614,627 A | 3/1997 | Takase et al. |
| 5,658,940 A | 8/1997 | Muller et al. |
| 5,698,579 A | 12/1997 | Muller |
| 5,703,098 A | 12/1997 | Muller et al. |
| 5,710,170 A | 1/1998 | Guay et al. |
| 5,728,844 A | 3/1998 | Muller et al. |
| 5,728,845 A | 3/1998 | Muller et al. |
| 5,736,570 A | 4/1998 | Muller et al. |
| 5,798,373 A | 8/1998 | Warrellow |
| 5,801,195 A | 9/1998 | Muller et al. |
| 5,849,770 A | 12/1998 | Head et al. |

(Continued)

FOREIGN PATENT DOCUMENTS

| EP | 0 347 146 | 6/1989 |
|---|---|---|
| EP | 0 349 239 A2 | 6/1989 |

(Continued)

OTHER PUBLICATIONS

Notice of Opposition dated May 26, 2010, in Opposition of EP Patent No. 1485087.
Patentee's Response to Notice of Opposition dated Oct. 29, 2010, in Opposition of EP Patent No. 1485087.
Decision with Minutes of the Oral Proceedings, dated May 19, 2011, in Opposition of EP Patent No. 1485087.
Patentee's Grounds of Appeal, dated Sep. 19, 2011, in Opposition of EP Patent No. 1485087.
Opponent's Response to Grounds of Appeal, dated Feb. 3, 2012, in Opposition of EP Patent No. 1485057.

(Continued)

*Primary Examiner* — Golam M M Shameem
(74) *Attorney, Agent, or Firm* — Jones Day

(57) ABSTRACT

Stereomerically pure (+)-2-[1-(3-Ethoxy-4-methoxyphenyl)-2-methylsulfonylethyl]-4-acetylaminoisoindoline-1,3-dione, substantially free of its (−) isomer, and prodrugs, metabolites, polymorphs, salts, solvates, hydrates, and clathrates thereof are discussed. Also discussed are methods of using and pharmaceutical compositions comprising the (+) enantiomer of 2-[1-(3-Ethoxy-4-methoxyphenyl)-2-methylsulfonylethyl]-4-acetylaminoisoindoline-1,3-dione are disclosed. The methods include methods of treating and/or preventing disorders ameliorated by the reduction of levels of TNF-α or the inhibition of PDE4.

24 Claims, 2 Drawing Sheets

(56) References Cited

U.S. PATENT DOCUMENTS

| | | | |
|---|---|---|---|
| 5,877,200 A | 3/1999 | Muller | |
| 5,891,896 A | 4/1999 | Warrellow et al. | |
| 6,011,050 A | 1/2000 | Muller et al. | |
| 6,020,339 A | 2/2000 | Perrier et al. | |
| 6,020,358 A | 2/2000 | Muller et al. | |
| 6,034,089 A | 3/2000 | Han et al. | |
| 6,046,221 A | 4/2000 | Muller et al. | |
| 6,069,156 A | 5/2000 | Oku et al. | |
| 6,162,830 A | 12/2000 | Connor et al. | |
| 6,166,041 A | 12/2000 | Cavalla et al. | |
| 6,177,471 B1 | 1/2001 | Menander et al. | |
| 6,204,275 B1 | 3/2001 | Friesen et al. | |
| 6,218,400 B1 | 4/2001 | Daugan et al. | |
| 6,300,335 B1 | 10/2001 | Campbell et al. | |
| 6,316,472 B1 | 11/2001 | Frenette et al. | |
| 6,333,354 B1 | 12/2001 | Schudt | |
| 6,962,940 B2 | 11/2005 | Muller et al. | |
| 7,208,516 B2 * | 4/2007 | Muller et al. | 514/417 |
| 7,276,529 B2 | 10/2007 | Muller et al. | |
| 7,358,272 B2 | 4/2008 | Muller et al. | |
| 7,427,638 B2 | 9/2008 | Muller et al. | |
| 7,507,759 B2 * | 3/2009 | Muller et al. | 514/417 |
| 7,659,302 B2 * | 2/2010 | Muller et al. | 514/417 |
| 7,659,303 B2 * | 2/2010 | Muller et al. | 514/417 |
| 8,455,536 B2 * | 6/2013 | Muller et al. | 514/417 |
| 8,802,717 B2 * | 8/2014 | Muller et al. | 514/417 |

FOREIGN PATENT DOCUMENTS

| | | |
|---|---|---|
| EP | 0 351 058 | 6/1989 |
| EP | 0 352 960 A2 | 7/1989 |
| EP | 0 395 328 | 4/1990 |
| EP | 0 428 268 A2 | 10/1990 |
| EP | 0 463 756 A1 | 6/1991 |
| EP | 0 526 004 A1 | 7/1992 |
| EP | 0 607 439 A1 | 9/1992 |
| EP | 0 722 937 A1 | 1/1996 |
| EP | 0 722 943 A1 | 1/1996 |
| EP | 0 722 944 A1 | 1/1996 |
| EP | 1752148 B1 | 6/2010 |
| GB | 2 063 249 A | 6/1981 |
| WO | WO 93/07149 | 4/1993 |
| WO | WO 93/12095 | 6/1993 |
| WO | WO 94/01728 | 1/1994 |
| WO | WO 94/05661 | 3/1994 |
| WO | WO 94/29277 | 12/1994 |
| WO | WO 95/19978 | 7/1995 |
| WO | WO 96/32379 | 10/1996 |
| WO | WO 97/03070 | 1/1997 |
| WO | WO 97/03675 | 2/1997 |
| WO | WO 97/03985 | 2/1997 |
| WO | WO 97/24334 | 7/1997 |
| WO | WO 98/06722 | 2/1998 |
| WO | WO 98/08848 | 3/1998 |
| WO | WO 98/14448 | 4/1998 |
| WO | WO 98/16521 | 4/1998 |
| WO | WO 98/17668 | 4/1998 |
| WO | WO 98/23597 | 6/1998 |
| WO | WO 98/38168 | 9/1998 |
| WO | WO 99/06041 | 2/1999 |
| WO | WO 00/25777 A1 | 5/2000 |

OTHER PUBLICATIONS

Patentee's Response dated Jun. 25, 2012, in Opposition of EP Patent No. Patent No. 1485057; and revised Annex A, dated Jan. 16, 2013.
Opponent's response to Summons to attend Oral Proceedings dated Feb. 3, 2015, in Opposition to EP Patent No. 1485087.
Patentee's Response to Summons to attend Oral Proceedings dated Feb. 16, 2015, in Opposition to EP Patent No. 1485087.
Decision of the Appeal Board with Minutes of the Oral Proceedings, Mar. 17, 2015, in Opposition to EP Patent No. 1485087.
Patentee's Petition for Review by Enlarged Appeal Board, dated Sep. 30, 2015, in Opposition to EP Patent No. 1485087.
Celgene press release, "Apremilast ESTEEM program meets primary and major secondary endpoint in pivotal phase III psoriasis trials," dated Jan. 7, 2013.
Celgene press release, "Positive phase IIB topline clinical data for Celgene oral compound apremilast (CC-10004) reported for patients with moderate-to-severe psoriasis," Dec. 15, 2009.
Chemistry in Britain, "Side-effects kill new prozac," p. 11 (2000).
European Commission's Decision to grant Marketing Authorization for Otezla, dated Jan. 15, 2015.
Gottlieb et al., "An open-label, single-arm pilot study in patients with severe plaque-type psoriasis treated with an oral anti-inflammatory agent, apremilast," Current Medical Research and Opinion, 24(5):1529-1538 (2008).
Lorenz et al., "Perspectives for TNF-α-targeting therapies," Arthritis Res., 4(suppl 3):S17-S24 (2002).
Papp et al., "Oral apremilast is active in the treatment of moderate to severe placque psoriasis," J. Am. Acad. Dermatol., P3308 (2011).
Poole et al., "Apremilast: first global approval," Drugs, 825-837 (2014).
Strand et al., "Improvede quality of life with apremilast (APR) in the treatment of psoriasis: results from a phase IIb randomized controlled study," J. Am. Acad. Dermatol., P3337 (2011).
Summary of Product Characteristics (Otezla) dated Feb. 16, 2015.
Tencer et al., "Economic evaluation of sequencing strategies in the treatment of moderate to severe psoriasis in the United States," EADV (2014).
Guillory, "Generation of polymophs, hydrates, solvates, and amorphous solids," in Polymoprhis in Pharmaceuticals Solids, Ed. H. G. Brittain, Marcel Dekker, Inc., New York, NY, pp. 183-226 (1999).
U.S. Appl. No. 60/454,155, filed Mar. 12, 2003, Miller, G. et al.
U.S. Appl. No. 60/454,149, filed Mar. 12, 2003, Muller, G. et al.
U.S. Appl. No. 60/438,448, filed Jan. 7, 2003, Muller, G. et al.
U.S. Appl. No. 60/436,975, filed Dec. 30, 2002, Muller, G. et al.
U.S. Appl. No. 60/366,515, filed Mar. 20, 2002, Muller, G. et al.
Akazome, M. et al., 1997, "Asymmetric recognition of 1-arylethylamines by (R)-phenylglycyl-(R)-phenylglycine and its mechanism," Tetrahedron: Asymmetry, Elsevier Scince Publishers, Amsterdam, NL, 8(14):2331-2336.
Au et al., 1998, "Effect of PDE4 inhibitors on zymosan-induced IL-8 release from human neutrophils: synergism with prostanoids and salbutamol," *Brit. J. Pharm.* 123:1260-1266.
Baehr et al., 1979, "Isolation and characterization of cGMP phosphodiesterase from bovine rod outer segments," *J. Biol. Chem.* 254:11669.
Baughman et al., 1990, "Release of tumor necrosis factor by alveolar macrophages of patients iwth sarcoidosis," *J Lab. Clin. Med.* 115:36-42.
Beavo and Reifsnyder, 1990 "Primary sequence of cyclic nucleotide phosphodiesterase isozymes and the design of selective inhibitors," *Trends in Pharm.*, 11:150-55.
Bissonnette et al., 1989, "Pulmonary inflammation and fibrosis in a murine model of asbestosis and silicosis. Possible role of tumor necrosis factor," *Inflammation* 13:329-339.
Bloom and Beavo 1996, "Identification and tissue-specific expression of PDE7 phosphodiesterase splice variants," *Proc. Natl. Acad. Sci. USA* 93:14188-14192.
Brackeen, M.F. et al., 1995, "Design and synthesis of conformationally constrained analogues of 4-(3-butoxy-4-methoxybenzyl) imidazolidin-2-one (Ro 20/1724) as potent inhibitors of cAMP-specific phosphodiesterase", *J. Med. Chem.* 38:4848-54.
Bryn et al., "Pharmaceutical solids: a strategic approach to regulatory considerations," *Pharm. Res.*, 12(7):945-954 (1995).
Carstensen, Jens T., 1995, *Drug Stability: Principles & Practice*, 2nd ed., Marcel Dekker, New York, NY pp. 379-380.
Casini et al., 1964, "Preparation of one of the optical antipodes of 2-phthalimidoglutarimide," Farmaco Ed. Sci. 19:563.
Clouse et al., 1989, "Monokine regulation of human immunodeficiency virus-1 expression in a chronically infected human T cell clone," *J. Immunol.* 142:431-438.
Caira, "Crystalline polymorphism of organic compounds," *Top. Curr. Chem.*, 198:163-208 (1998).

(56) References Cited

OTHER PUBLICATIONS

Derian et al., 1995, "Inhibition of chemotactic peptide-induced neutrophil adhesion to vascular endothelium by cAMP modulators," *J. Immunol.* 154:308-317.

Dredge et al., 2002, "Immunological effects of thalidomide and its chemical and functional analogs," *Crit. Rev. Immunol.* 22(5-6):425-437.

Dredge et al., 2002, "Recent developments in antiangiogenic therapy," *Expert Opin. Biol. Ther.* 2(8):953-966.

Dredge et al., 2003, "Angiogenesis inhibitors in cancer therapy," *Curr. Opin. Investig. Drugs* 4(6):667-674.

Duh et al., 1989, "Tumor necrosis factor alpha activates human immunodeficiency virus type 1 through induction of nuclear factor binding to the NF-kappa B sites in the long terminal repeat," *Proc. Nat. Acad. Sci.* 86:5974-5978.

Featherstone, R.L., et al., 2000, "Comparison of phosphodiesterase inhibitors of differing isoenzyme selectivity added to St. Thomas' hospital cardioplegic solution used for hypothermic preservation of rat lungs", *Am. J. Respir. Crit. Care Med.* 162:850-6.

Gee et al., 2003, "Selective cytokine inhibitory drugs with enhanced antiangiogenic activity control tumor growth through vascular inhibition," *Cancer Res.* 63(23):8073-8078.

Gillespie et al., 1989, "Inhibition and stimulation of photoreceptor phosphodiesterases by dipyridamole and M&B 22,948," *Mol. Pharm.* 36:773-781.

Grant, "Theory and origin of polymorphosim," in *Polymoprhis in Pharmaceuticals Solids*, Ed. H. G. Brittain, Marcel Dekker, Inc., New York, NY, pp. 1-33 (1999).

Hidaka and Asano 1976, "Human blood platelet 3': 5'-cyclic nucleotide phosphodiesterase. Isolation of low-Km and high-Km phosphodiesterase," *Biochem. Biophys. Acta* 429:485.

Hinshaw et al. 1990, "Survival of primates in LD100 septic shock following therapy with antibody to tumor necrosis factor (TNF alpha)," *Circ. Shock* 30:279-292.

Holler et al., 1990, "Increased serum levels of tumor necrosis factor alpha precede major complications of bone marrow transplantation," *Blood* 75:1011-1016.

Johnson et al., 1989, "Tumors producing human tumor necrosis factor induced hypercalcemia and osteoclastic bone resorption in nude mice," *Endocrinology* 124:1424-1427.

List et al., 1990, "The myelodysplastic syndromes: biology and implications for management," *J. Clin. Oncol.* 8:1424-1441.

Luke, G.P. et al., 1999, "Synthesis of (S)-5-(1-aminoethyl)-2-(cyclohexylmethoxy) benzamide," Tetrahedron: Asymmetry, Elsevier Science Publishers, Amsterdam, NL, 10(22):4393-4403.

Marriott et al., 2001, "Immunotherapeutic and antitumour potential of thalidomide analogues," *Expert Opin. Biol. Ther.* 1(4):1-8.

Marriott et al., 2002, "Thalidomide and its analogues have distinct and opposing effects on TNF-alpha and TNFR2 during co-stimulation of both CD4(+) and CD8(+) T cells," *Clin. Exp. Immunol.* 130(1):75-84.

Merck Manual (1999) $17^{th}$ ed., pp. 953.

Molostvov et al., 2004, "The effects of selective cytokine inhibitory drugs (CC-10004 and CC-1088) on VEGF and IL-6 expression and apoptosis in myeloma and endothelial cell co-cultures," *Br. J. Haematol.* 124(3):366-375.

Monté et al., 1992, "Productive human immunodeficiency virus-1 infection of megakaryocytic cells is enhanced by tumor necrosis factor-alpha,"*Blood* 79:2670-2679.

Muller et al., 1998, "Thalidomide analogs and PDE4 inhibition," *Bioorg. & Med Chem Lett.* 8:2669-2674.

Muller, et al., 1996, "Structural modifications of thalidomide produce analogs with enhanced tumor necrosis factor inhibitory activity," *J. Med. Chem.* 39:3238-3240.

Muller, George, et al., 1999, "Amino-substituted thalidomide analogs: potent inhibitors of TNF-alpha production.," *Bioorganic & Medicinal Chemistry Letters* 9:1625-1630.

Nicholson et al., 1991, "Differential modulation of tissue function and therapeutic potential of selective inhibitors of cyclic nucleotide phosphodiesterase isoenzymes," *Trends Pharmaco. Sci.* 12:19-27.

Shealy et al., 1965, "D- and L-thalidomide." *Chem. Indus.* 12;24:1030-1031.

Tierney, et al., ed., 1998, Current Medical Diagnosis & Treatment, $37^{th}$ ed., Appleton & Lange, pp. 499.

Van Dullemen et al., 1995, "Treatment of Crohn's disease with anti-tumor necrosis factor chimeric monoclonal antibody (cA2)," *Gastroenterology*, 109:129-135.

Verghese, et al.,1995, "Differential regulation of human monocyte-derived TNF alpha and IL-1 beta by type IV cAMP-phosphodiesterase (cAMP-PDE) inhibitors," *J. Pharmacol. Exp. Ther.*, 272(3), 1313-1320.

Wilen, S.H., 1972, *Tables of Resolving Agents and Optical Resoutions* (E.L. Eliel, Ed., Univ. of Notre Dame Press, Notre Dame, IN) p. 268.

Wilen, S.H., et al., 1977, "Strategies in optical resolutions," *Tetrahedron* 33:2725-2736.

Wolff, Manfred E., ed., *Burger's Medicinal Chemistry and Drug Discovery*, $5^{th}$ ed. 1995 172-178, 949-982.

\* cited by examiner

METHODS OF USING (+)-2-[1-(3-ETHOXY-4-METHOXYPHENYL)-2-METHYLSULFONYLETHYL]-4-ACETYLAMINOISOINDOLINE-1,3-DIONE

This application is a continuation application of U.S. patent application Ser. No. 13/682,652, filed Nov. 20, 2012, which is a continuation application of U.S. patent application Ser. No. 12/630,788, filed Dec. 3, 2009, now U.S. Pat. No. 8,455,536, which is a continuation application of U.S. patent application Ser. No. 12/098,379, filed Apr. 4, 2008, now U.S. Pat. No. 7,659,303, which is a divisional application of U.S. patent application Ser. No. 11/170,308, filed Jun. 28, 2005, now U.S. Pat. No. 7,358,272, which is a divisional application of U.S. patent application Ser. No. 10/392,195, filed Mar. 19, 2003, now U.S. Pat. No. 6,962,940, which claims the benefit of U.S. Provisional Application No. 60/366,515 filed Mar. 20, 2002 and U.S. Provisional Application No. 60/438,450 filed Jan. 7, 2003, all of which are incorporated herein by reference in their entireties.

FIELD OF INVENTION

The invention relates to methods of using and compositions comprising the (+) enantiomer of 2-[1-(3-Ethoxy-4-methoxyphenyl)-2-methylsulfonylethyl]-4-acetylaminoisoindoline-1,3-dione.

BACKGROUND OF THE INVENTION

Tumor necrosis factor alpha, (TNF-α) is a cytokine that is released primarily by mononuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. But TNF-α also has a role in many diseases. When administered to mammals or humans, TNF-α causes or aggravates inflammation, fever, cardiovascular effects, hemorrhage, coagulation, and acute phase responses similar to those seen during acute infections and shock states. Enhanced or unregulated TNF-α production has been implicated in a number of diseases and medical conditions, for example, cancers, such as solid tumors and blood-born tumors; heart disease, such as congestive heart failure; and viral, genetic, inflammatory, allergic, and autoimmune diseases.

Adenosine 3',5'-cyclic monophosphate (cAMP) also plays a role in many diseases and conditions, such as but not limited to asthma and inflammation, and other conditions (Lowe and Cheng, *Drugs of the Future*, 17 (9), 799-807, 1992). It has been shown that the elevation of cAMP in inflammator leukocytes inhibits their activation and the subsequent release of inflammatory mediators, including TNF-α and NF-κB. Increased levels of cAMP also leads to the relaxation of airway smooth muscle.

It is believed that the primary cellular mechanism for the inactivation of cAMP is the breakdown of cAMP by a family of isoenzymes referred to as cyclic nucleotide phosphodiesterases (PDE) (Beavo and Reitsnyder, *Trends in Pharm.*, 11, 150155, 1990). There are eleven known PDE families. It is recognized, for example, that the inhibition of PDE type IV is particularly effective in both the inhibition of inflammatory mediator release and the relaxation of airway smooth muscle (Verghese, et al., *Journal of Pharmacology and Experimental Therapeutics*, 272 (3), 1313-1320, 1995). Thus, compounds that inhibit PDE4 (PDE IV) specifically, may inhibit inflammation and aid the relaxation of airway smooth muscle with a minimum of unwanted side effects, such as cardiovascular or anti-platelet effects. Currently used PDE4 inhibitors lack the selective action at acceptable therapeutic doses.

Cancer is a particularly devastating disease, and increases in blood TNF-α levels are implicated in the risk of and the spreading of cancer. Normally, in healthy subjects, cancer cells fail to survive in the circulatory system, one of the reasons being that the lining of blood vessels acts as a barrier to tumor-cell extravasation. But increased levels of cytokines have been shown to substantially increase the adhesion of cancer cells to endothelium in vitro. One explanation is that cytokines, such as TNF-α, stimulate the biosynthesis and expression of a cell surface receptors called ELAM-1 (endothelial leukocyte adhesion molecule). ELAM-1 is a member of a family of calcium-dependent cell adhesion receptors, known as LEC-CAMs, which includes LECAM-1 and GMP-140. During an inflammatory response, ELAM-1 on endothelial cells functions as a "homing receptor" for leukocytes. Recently, ELAM-1 on endothelial cells was shown to mediate the increased adhesion of colon cancer cells to endothelium treated with cytokines (Rice et al., 1989, *Science* 246:1303-1306).

Inflammatory diseases such as arthritis, related arthritic conditions (e.g., osteoarthritis and rheumatoid arthritis), inflammatory bowel disease (e.g., Crohn's disease and ulcerative colitis), sepsis, psoriasis, atopic dermatitis, contact dermatitis, and chronic obstructive pulmonary disease, chronic inflammatory pulmonary diseases are also prevalent and problematic ailments. TNF-α plays a central role in the inflammatory response and the administration of their antagonists block chronic and acute responses in animal models of inflammatory disease.

Enhanced or unregulated TNF-α production has been implicated in viral, genetic, inflammatory, allergic, and autoimmune diseases. Examples of such diseases include but are not limited to: HIV; hepatitis; adult respiratory distress syndrome; bone-resorption diseases; chronic obstructive pulmonary diseases; chronic pulmonary inflammatory diseases; asthma, dermatitis; cystic fibrosis; septic shock; sepsis; endotoxic shock; homodynamic shock; sepsis syndrome; post ischemic reperfusion injury; meningitis; psoriasis; fibrotic disease; cachexia; graft rejection; auto-immune disease; rheumatoid spondylitis; arthritic conditions, such as rheumatoid arthritis and osteoarthritis; osteoporosis; Crohn's disease; ulcerative colitis; inflammatory-bowel disease; multiple sclerosis; systemic lupus erythrematosus; ENL in leprosy; radiation damage; asthma; and hyperoxic alveolar injury. Tracey et al., 1987, *Nature* 330:662-664 and Hinshaw et al., 1990, *Circ. Shock* 30:279-292 (endotoxic shock); Dezube et al., 1990, *Lancet*, 335:662 (cachexia); Millar et al., 1989, *Lancet* 2:712-714 and Ferrai-Baliviera et al., 1989, *Arch. Surg.* 124:1400-1405 (adult respiratory distress syndrome); Bertolini et al., 1986, *Nature* 319:516-518, Johnson et al., 1989, *Endocrinology* 124:1424-1427, Holler et al., 1990, *Blood* 75:1011-1016, and Grau et al., 1989, *N. Engl. J. Med.* 320:1586-1591 (bone resorption diseases); Pignet et al., 1990, *Nature*, 344:245-247, Bissonnette et al., 1989, *Inflammation* 13:329-339 and Baughman et al., 1990, *J. Lab. Clin. Med.* 115:36-42 (chronic pulmonary inflammatory diseases); Elliot et al., 1995, *Int. J. Pharmac.* 17:141-145 (rheumatoid arthritis); von Dullemen et al., 1995, *Gastroenterology*, 109: 129-135 (Crohn's disease); Duh et al., 1989, *Proc. Nat. Acad. Sci.* 86:5974-5978, Poll et al., 1990, *Proc. Nat. Acad. Sci.* 87:782-785, Monto et al., 1990, *Blood* 79:2670, Clouse et al., 1989, *J. Immunol.* 142, 431-438, Poll et al., 1992, *AIDS Res. Hum. Retrovirus*, 191-197, Poli et al. 1990, *Proc. Natl. Acad.*

Sci. 87:782-784, Folks et al., 1989, PNAS 86:2365-2368 (HIV and opportunistic infections resulting from HIV).

Pharmaceutical compounds that can block the activity or inhibit the production of certain cytokines, including TNF-α, may be beneficial therapeutics. Many small-molecule inhibitors have demonstrated an ability to treat or prevent inflammatory diseases implicated by TNF-α (for a review, see Lowe, 1998 *Exp. Opin. Ther. Patents* 8:1309-1332). One such class of molecules are the substituted phenethylsulfones described in U.S. Pat. No. 6,020,358.

SUMMARY OF THE INVENTION

This invention relates to methods of treating diseases and disorders utilizing an enantiomer of a substituted phenethylsulfone compound and pharmaceutically acceptable salts, hydrates, solvates, clathrates, prodrugs and polymorphs thereof and methods for reducing the level of cytokines and their precursors in mammals. The invention also relates to pharmaceutical compositions comprising an enantiomer of 2-[1-(3-Ethoxy-4-methoxyphenyl)-2-methylsulfonylethyl]-4-acetylaminoisoindoline-1,3-dione and a pharmaceutically acceptable carrier. The invention further relates to an enantiomer of 2-[1-(3-Ethoxy-4-methoxyphenyl)-2-methylsulfonylethyl]-4-acetylaminoisoindoline-1,3-dione substantially free of its other enantiomer.

This invention particularly relates to the (+) enantiomer of 2-[1-(3-Ethoxy-4-methoxyphenyl)-2-methylsulfonylethyl]-4-acetylaminoisoindoline-1,3-dione. This compound is believed to have increased potency and other benefits as compared to its racemate—2-[1-(3-Ethoxy-4-methoxyphenyl)-2-methylsulfonylethyl]-4-acetylaminoisoindoline-1,3-dione.

The invention encompasses the use of the (+) enantiomer of 2-[1-(3-Ethoxy-4-methoxyphenyl)-2-methylsulfonylethyl]-4-acetylaminoisoindoline-1,3-dione for treating or preventing diseases or disorders ameliorated by the inhibition of TNF-α production in mammals. In certain embodiments, this treatment includes the reduction or avoidance of adverse effects. Such disorders include, but are not limited to, cancers, including, but not limited to cancer of the head, thyroid, neck, eye, skin, mouth, throat, esophagus, chest, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof. Specific cancers that can be treated by this method are multiple myeloma, malignant melanoma, malignant glioma, leukemia and solid tumors.

The invention also encompasses the use of the (+) enantiomer of 2-[1-(3-Ethoxy-4-methoxyphenyl)-2-methylsulfonylethyl]-4-acetylaminoisoindoline-1,3-dione in the treatment or prevention of heart disease, including, but not limited to congestive heart failure, cardiomyopathy, pulmonary edema, endotoxin-mediated septic shock, acute viral myocarditis, cardiac allograft rejection, and myocardial infarction.

The invention also encompasses the use of the (+) enantiomer of 2-[1-(3-Ethoxy-4-methoxyphenyl)-2-methylsulfonylethyl]-4-acetylaminoisoindoline-1,3-dione to treat diseases or disorders ameliorated by the inhibition of PDE4. For example, the compounds and compositions of the invention may be useful to treat or prevent viral, genetic, inflammatory, allergic, and autoimmune diseases. Examples of such diseases include, but are not limited to: HIV; hepatitis; adult respiratory distress syndrome; bone-resorption diseases; chronic obstructive pulmonary diseases; chronic pulmonary inflammatory diseases; dermatitis; inflammatory skin disease, atopic dermatitis, cystic fibrosis; septic shock; sepsis; endotoxic shock; hemodynamic shock; sepsis syndrome; post ischemic reperfusion injury; meningitis; psoriasis; fibrotic disease; cachexia; graft rejection including graft versus host disease; auto-immune disease; rheumatoid spondylitis; arthritic conditions, such as rheumatoid arthritis and osteoarthritis; osteoporosis; Crohn's disease; ulcerative colitis; inflammatory-bowel disease; multiple sclerosis; systemic lupus erythrematosus; erythema nodosum leprosum (ENL) in leprosy; radiation damage; asthma; and hyperoxic alveolar injury.

In yet another embodiment, the stereomerically pure (+) enantiomer of 2-[1-(3-Ethoxy-4-methoxyphenyl)-2-methylsulfonylethyl]-4-acetylaminoisoindoline-1,3-dione is also useful in the treatment or prevention of microbial infections or the symptoms of microbial infections including, but not limited to, bacterial infections, fungal infections, malaria, mycobacterial infection, and opportunistic infections resulting from HIV.

The invention further encompasses pharmaceutical compositions and single unit dosage forms comprising an enantiomer of 2-[1-(3-Ethoxy-4-methoxyphenyl)-2-methylsulfonylethyl]-4-acetylaminoisoindoline-1,3-dione and pharmaceutically acceptable polymorphs, prodrugs, salts, hydrates, clathrates, and solvates thereof.

In a separate embodiment, the invention encompasses the (+) enantiomer of 2-[1-(3-Ethoxy-4-methoxyphenyl)-2-methylsulfonylethyl]-4-acetylaminoisoindoline-1,3-dione.

In a further embodiment, the invention encompasses a method of producing a stereomerically pure enantiomer of 2-[1-(3-Ethoxy-4-methoxyphenyl)-2-methylsulfonylethyl]-4-acetylaminoisoindoline-1,3-dione which comprises contacting 1-(3-Ethoxy-4-methoxy-phenyl)-2-methanesulfonyl-ethylamine with a chiral amino acid and contacting the product of the first step with N-(1,3-Dioxo-1,3-dihydro-isobenzofuran-4-yl)-acetamide. In a related embodiment, the invention encompasses a chiral salt of 1-(3-Ethoxy-4-methoxy-phenyl)-2-methanesulfonyl-ethylamine.

DEFINITIONS

Figure 1:
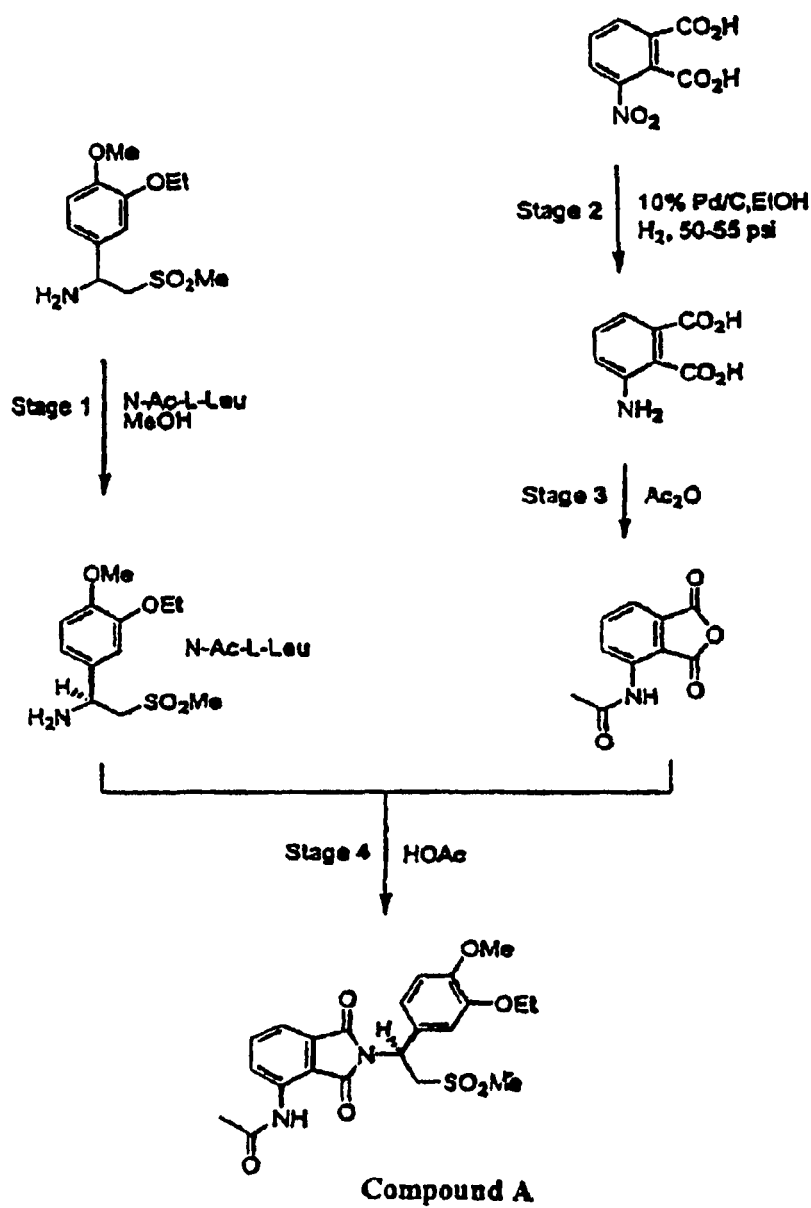
FIG. 1. illustrates the preparation of the (+) enantiomer of 2-[1-(3-Ethoxy-4-methoxyphenyl)-2-methylsulfonylethyl]-4-acetylaminoisoindoline-1,3-dione.
Figure 2:
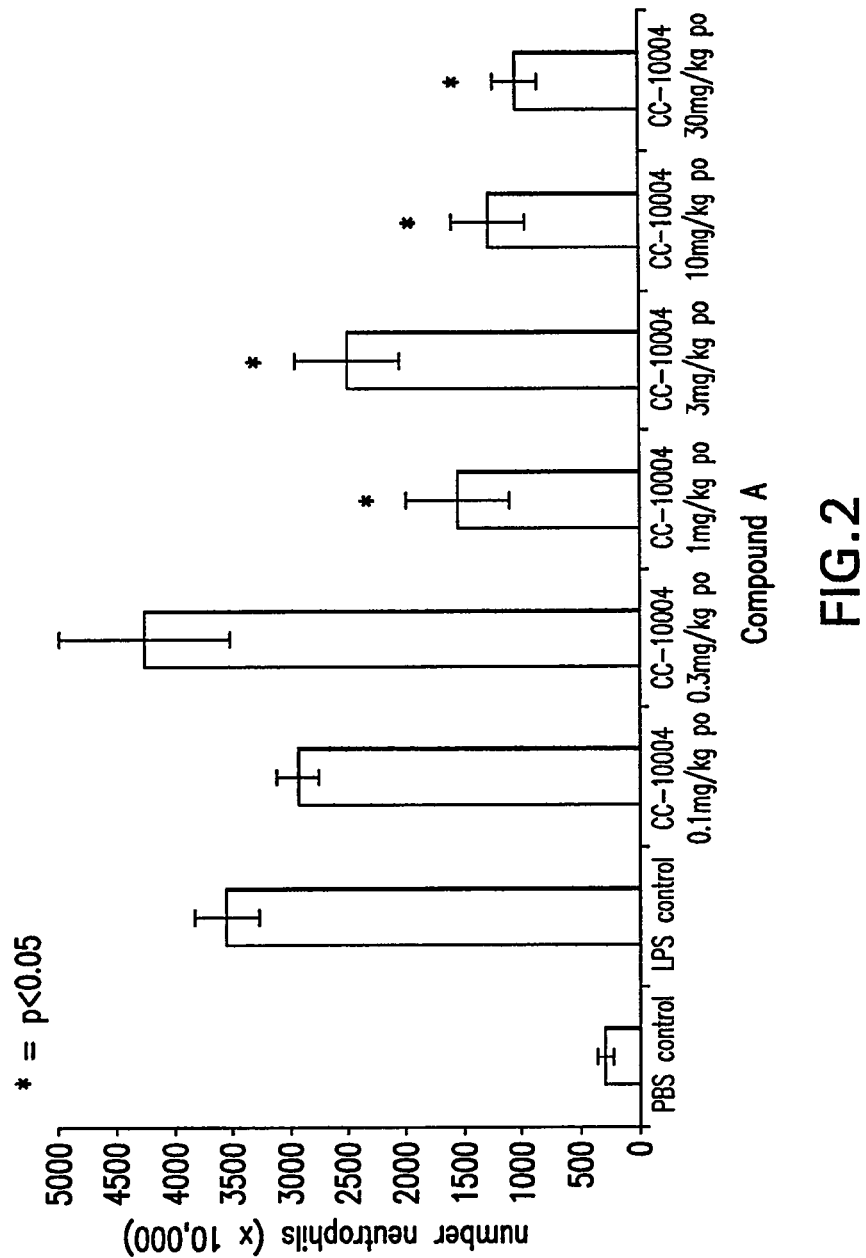
FIG. 2. illustrates the effect of the enantiomer of the invention on LPS-induced neutrophilia in the lungs of conscious ferrets.

As used herein, term "Compound A" refers to an enantiomerically pure form of 2-[1-(3-ethoxy-4-meth-4 oxyphenyl)-2-methylsulfonylethyl]-4-acetylaminoisoindoline-1,3-dione which comes off of an HPLC column at about 25.4 minutes when that column is a 150 mm×4.6 mm Ultron Chiral ES-OVS chiral HPLC column (Agilent Technology), the eluent is 15:85 ethanol: 20 mM $KH_2PO_4$ at pH 3.5, and the observation wavelength is 240 nm. The $^1H$ NMR spectrum of compound A is substantially as follows: δ($CDCl_3$): 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H). The $^{13}C$ NMR spectrum of Compound A is substantially as follows δ(DMSO-$d_6$): 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48. Compound A dissolved in methanol also rotates plane polarized light in the (+) direction.

Without being limited by theory, Compound A is believed to be S-{2-[1-(3-ethoxy-4-methoxyphenyl)-2-methylsulfonylethyl]-4-acetylaminoisoindoline-1,3-dione}, which has the following structure:

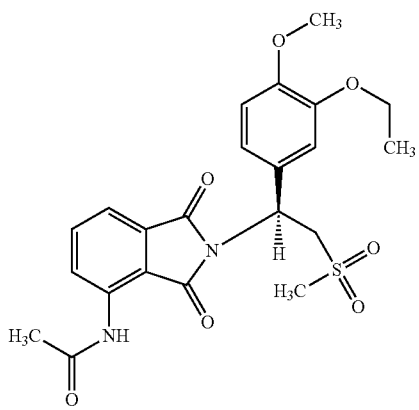

As used herein, the term "patient" refers to a mammal, particularly a human.

As used herein, the term "pharmaceutically acceptable salts" refer to salts prepared from pharmaceutically acceptable non-toxic acids or bases including inorganic acids and bases and organic acids and bases. Suitable pharmaceutically acceptable base addition salts for the compound of the present invention include metallic salts made from aluminum, calcium, lithium, magnesium, potassium, sodium and zinc or organic salts made from lysine, N,N'-dibenzyethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of Compound A that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 *Burger's Medicinal Chemistry and Drug Discovery,* 172-178, 949-982 (Manfred E. Wolff ed., 5th ed. 1995).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein, term "adverse effects" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

As used herein and unless otherwise indicated, the phrases "reduce or avoid adverse effects" and "reducing or avoiding adverse effects" mean the reduction of the severity of one or more adverse effects as defined herein.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

DETAILED DESCRIPTION OF THE INVENTION

This invention relates to stereomerically pure Compound A, which is an enantiomer of 2-[1-(3-Ethoxy-4-methoxphenyl)-2-methyl sulfonylethyl]-4-acetylaminoisoindotine-1,3-dione, substantially free of its other enantiomer, as well as novel methods using, and compositions comprising stereomerically pure Compound A. For example, the present invention encompasses the in vitro and in vivo use of Compound A, and the incorporation of Compound A into pharmaceutical compositions and single unit dosage forms useful in the treatment and prevention of a variety of diseases and disorders. Diseases and disorders which are ameliorated by the reduction of levels of TNF-α or inhibition of PDE4 are well known in the art and are described herein. Specific methods of the invention reduce or avoid the adverse effects associated with compounds used as TNF-α inhibitor. Other specific methods of the invention reduce or avoid the adverse effects associated with use of racemic 2-[1-(3-Ethoxy-4-methoxyphenyl)-2-methylsulfonylethyl]-4-acetylaminoisoindoline-1,3-dione.

Specific methods of the invention include methods of treating or preventing diseases and disorders including, but not limited to, solid tumor cancers, blood-born cancers and inflammatory diseases.

Pharmaceutical and dosage forms of the invention, which comprise Compound A or a pharmaceutically acceptable polymorph, prodrug, salt, clathrate, solvate or hydrate thereof, can be used in the methods of the invention.

Without being limited by theory, it is believed that Compound A can inhibit TNF-α production. Consequently, a first embodiment of the invention relates to a method of inhibiting TNF-α production which comprises contacting a cell exhibiting abnormal TNF-α production with an effective amount of stereomerically pure Compound A, or a pharmaceutically acceptable prodrug, metabolite, polymorph, salt, solvate, hydrate, or clathrate thereof. In a particular embodiment, the invention relates to a method of inhibiting TNF-α production which comprises contacting a mammalian cell exhibiting abnormal TNF-α production with an effective amount of stereomerically pure Compound A, or a pharmaceutically acceptable prodrug, metabolite, polymorph, salt, solvate, hydrate, or clathrate thereof.

The invention also relates to a method of treating or preventing disorders ameliorated by the reduction of levels of TNF-α in a patient which comprises administering to a patient in need of such treatment or prevention a therapeutically or prophylactically effective amount of stereomerically pure compound A, or a pharmaceutically acceptable prodrug, metabolite, polymorph, salt, solvate, hydrate, or clathrate thereof.

A further embodiment of the invention relates to a method of treating or preventing cancer, including but not limited to, solid tumor, blood-born tumor, leukemias, and in particular, multiple myeloma in a patient which comprises administering to a patient in need of such treatment or prevention a therapeutically effective amount of stereomerically pure compound A, or a pharmaceutically acceptable prodrug, metabolite, polymorph, salt, solvate, hydrate, or clathrate thereof; in particular wherein the patient is a mammal.

In another embodiment, the invention relates to a method of inhibiting PDE4 which comprises contacting PDE4 with an effective amount of stereomerically pure Compound A, or a pharmaceutically acceptable prodrug, metabolite, polymorph, salt, solvate, hydrate, or clathrate thereof.

In another embodiment, the invention relates to a method of controlling cAMP levels in a cell which comprises contacting a cell with an effective amount of stereomerically pure Compound A, or a pharmaceutically acceptable prodrug, metabolite, polymorph, salt, solvate, hydrate, or clathrate thereof. As used herein the term "controlling cAMP levels" includes preventing or reducing the rate of the breakdown of Adenosine 3',5'-cyclic monophosphate (cAMP) in a cell or increasing the amount of Adenosine 3',5'-cyclic monophosphate present in a cell, preferably a mammalian cell, more preferably a human cell. In a particular method, the rate of cAMP breakdown is reduced by about 10, 25, 50, 100, 200, or 500 percent as compared to the rate in comparable cells which have not been contacted with a compound of the invention.

A further embodiment of the invention relates to a method of treating or preventing diseases or disorders ameliorated by the inhibition of PDE4 in a patient which comprises administering to a patient in need of such treatment or prevention a therapeutically or prophylactically effective amount of stereomerically pure Compound A, or a pharmaceutically acceptable prodrug, metabolite, polymorph, salt, solvate, hydrate, or clathrate thereof. Disorders ameliorated by the inhibition of PDE4 include, but are not limited to, asthma, inflammation (e.g., inflammation due to reperfusion), chronic or acute obstructive pulmonary diseases, chronic or acute pulmonary inflammatory diseases, inflammatory bowel disease, Crohn's Disease, Bechet's Disease, or colitis.

A further embodiment of the invention relates to a method of treating or preventing depression, asthma, inflammation (e.g., contact dermatitis, atopic dermatitis, psoriais, rheumatoid arthritis, osteoarthritis, inflammatory skin disease, inflammation due to reperfusion), chronic or acute obstructive pulmonary diseases, chronic or pulmonary inflammatory diseases, inflammatory bowel disease, Crohn's Disease, Bechet's Disease or colitis in a patient which comprises administering to a patient in need of such treatment or prevention a therapeutically or prophylactically effective amount of stereomerically pure Compound A, or a pharmaceutically acceptable prodrug, metabolite, polymorph, salt, solvate, hydrate, or clathrate thereof; in particular wherein the patient is a mammal.

A separate embodiment of the invention encompasses methods of treating or preventing Myelodysplastic syndrome (MDS) which comprises administering to a patient in need of such treatment or prevention a therapeutically or prophylactically effective amount of stereomerically pure Compound A, or a pharmaceutically acceptable salt, solvate, hydrate, stereoisomer, clathrate, or prodrug thereof. MDS refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production. See The Merck Manual 953 (17th ed. 1999) and List et al., 1990, *J. Clin. Oncol.* 8:1424.MDS A separate embodiment of the invention encompasses methods of treating or preventing Myeloproliferative disease (MPD) which comprises administering to a patient in need of such treatment or prevention a therapeutically or prophylactically effective amount of stereomerically pure Compound A, or a pharmaceutically acceptable salt, solvate, hydrate, stereoisomer, clathrate, or prodrug thereof. Myeloproliferative disease (MPD) refers to a group of disorders characterized by clonal abnormalities of the hematopoietic stem cell. See e.g., Current Medical Diagnosis & Treatment, pp. 499 (37th ed., Tierney et al. ed, Appleton & Lange, 1998).

The invention also encompasses a method of treating, preventing or managing complex regional pain syndrome, which comprises administering to a patient in need of such treatment, prevention or management a therapeutically or prophylactically effective amount of a stereomerically pure Compound A, or a pharmaceutically acceptable salt, solvate, hydrate, stereoisomer, clathrate, or prodrug thereof. In a specific embodiment, the administration is before, during or after surgery or physical therapy directed at reducing or avoiding a symptom of complex regional pain syndrome in the patient.

In particular methods of the invention, stereomerically pure Compound A, or a pharmaceutically acceptable polymorph, prodrug, salt, solvate, hydrate, or clathrate thereof, is adjunctively administered with at least one additional therapeutic agent. Examples of additional therapeutic agents include, but are not limited to, anti-cancer drugs, anti-inflammatories, antihistamines and decongestants.

Synthesis and Preparation

Racemic 2-[1-(3-Ethoxy-4-methoxyphenyl)-2-methylsulfonylethyl]-4-acetylaminoisoindoline-1,3-dione is readily prepared using the methods in U.S. Pat. No. 6,020,358, which is incorporated herein by reference.

Compound A can be isolated from the racemic compound by techniques known in the art. Examples include, but are not limited to, the formation of chiral salts and the use of chiral or high performance liquid chromatography "HPLC" and the formation and crystallization of chiral salts. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

In a specific method, Compound A is synthesized from 3-acetamidophthalic anhydride and a chiral amino acid salt of (S)-2-(3-ethoxy-4-methoxyphenyl)-1-(methylsulphonyl)-eth-2-ylamine. Chiral amino acid salts of (S)-2-(3-ethoxy-4-methoxyphenyl)-1-(methylsulphonyl)-eth-2-ylamine include, but not limited to salts formed with the L isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2 amino isobutyric acid, 3 amino propionic acid, ornithine, norleucine, norvaline, hydroxyproline, sarcosine, citrulline, cysteic acid, t-butylglycine, t-butylalanine, phenylglycine, cyclohexylalanine, and N-acetyl-leucine. A specific chiral amino acid salt is (S)-2-(3-ethoxy-4-methoxyphenyl)-1-(methylsulphonyl)-eth-2-ylamine N-acetyl-L-leucine salt, which is resolved from 2-(3-ethoxy-4-methoxyphenyl)-1-(methylsulphonyl)-eth-2-ylamine and N-acetyl-L-leucine in methanol.

Methods of Treatment

The invention encompasses methods of treating and preventing diseases or disorders ameliorated by the reduction of levels of TNF-α in a patient which comprise administering to a patient in need of such treatment or prevention a therapeutically effective amount of stereomerically pure Compound A, or a pharmaceutically acceptable prodrug, metabolite, polymorph, salt, solvate, hydrate, or clathrate thereof.

Disorders ameliorated by the inhibition of TNF-α include, but are not limited to: heart disease, such as congestive heart failure, cardiomyopathy, pulmonary edema, endotoxin-mediated septic shock, acute viral myocarditis, cardiac allograft rejection, and myocardial infarction; solid tumors, including but not limited to, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, and retinoblastoma; and blood-born tumors including but not limited to, acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma and acute and chronic leukemias, for example, lymphoblastic, myelogenous, lymphocytic, and myelocytic leukemias.

Specific methods of the invention further comprise the administration of an additional therapeutic agent (i.e., a therapeutic agent other than Compound A). Examples of additional therapeutic agents include, but are not limited to, anti-cancer drugs such as, but are not limited to: alkylating agents, nitrogen mustards, ethylenimines, methylmelamines, alkyl sulfonates, nitrosoureas, triazenes, folic acid analofs, pyrimidine analogs, purine analogs, vinca alkaloids, epipodophyllotoxins, antibiotics, topoisomerase inhibitors and anti-cancer vaccines.

Specific additional therapeutic agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper, mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor, bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor, interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor, leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor, platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur;

tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

The invention further encompasses a method of treating or preventing diseases or disorders ameliorated by the inhibition of PDE4 in a patient which comprise administering to a patient in need of such treatment or prevention a therapeutically effective amount of stereomerically pure Compound A, or a pharmaceutically acceptable prodrug, metabolite, polymorph, salt, solvate, hydrate, or clathrate thereof. Disorders ameliorated by the inhibition of PDE4 include, but are not limited to, asthma, inflammation, chronic or acute obstructive pulmonary disease, chronic or acute pulmonary inflammatory disease, inflammatory bowel disease, Crohn's Disease, Bechet's Disease, colitis, ulcerative colitis and arthritis or inflammation due to reperfusion. In a preferred embodiment, the disease or disorder to be treated or prevented is chronic obstructive pulmonary disease.

Specific methods of the invention can comprise the administration of an additional therapeutic agent such as, but not limited to, anti-inflammatory drugs, antihistamines and decongestants. Examples of such additional therapeutic agents include, but are not limited to: antihistamines including, but not limited to, ethanolamines, ethylenediamines, piperazines, and phenothiazines; antinflammatory drugs; NSAIDS, including, but not limited to, aspirin, salicylates, acetominophen, indomethacin, sulindac, etodolac, fenamates, tolmetin, ketorolac, diclofenac, ibuprofen, naproxen, fenoprofen, ketoprofen, flurbiprofen, oxaprozin, piroxicam, meloxicam, pyrazolon derivatives; and steriods including, but not limited to, cortical steroids and adrenocortical steroids.

Specific methods of the invention avoid or reduce drug-drug interactions and other adverse effects associated with agents used in the treatment of such disorders, including racemic substituted phenylethylsulfones. Without being limited by any theory, stereomerically pure Compound A may further provide an overall improved therapeutic effectiveness, or therapeutic index, over racemic 2-[1-(3-Ethoxy-4-methoxyphenyl)-2-methylsulfonylethyl]-4-acetylaminoisoindoline-1,3-dione. For example, a smaller amount of the drug may in some circumstances be administered to attain the same level of effectiveness.

As stated above, the active compound of the invention (i.e., Compound A) may be used in the treatment or prevention of a wide range of diseases and conditions. The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg to about 1000 mg per day, given as a single once-a-day dose preferably as divided doses throughout a day. More specifically, the daily dose is administered twice daily in equally divided doses. Specifically, a daily dose range should be from about 5 mg to about 500 mg per day, more specifically, between about 10 mg and about 200 mg per day. Specifically, the daily dose may be administered in 5 mg, 10 mg, 15 mg, 20 mg, 25 mg, 50 mg, or 100 mg dosage forms. In managing the patient, the therapy should be initiated at a lower dose, perhaps about 1 mg to about 25 mg, and increased if necessary up to about 200 mg to about 1000 mg per day as either a single dose or divided doses, depending on the patient's global response. Alternatively, the daily dose is from 0.01 mg/kg to 100 mg/kg.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

The phrases "therapeutically effective amount", "prophylactically effective amount" and "therapeutically or prophylactically effective amount," as used herein encompasses the above described dosage amounts and dose frequency schedules. Different therapeutically effective amounts may be applicable for different diseases and conditions, as will be readily known by those of ordinary skill in the art. Similarly, amounts sufficient to treat or prevent such disorders, but insufficient to cause, or sufficient to reduce, adverse effects associated with racemic 2-[1-(3-Ethoxy-4-methoxyphenyl)-2-methylsulfonylethyl]-4-acetylaminoisoindoline-1,3-dione are also encompassed by the above described dosage amounts and dose frequency schedules.

Pharmaceutical Compositions

Pharmaceutical compositions and single unit dosage forms comprising Compound A, or a pharmaceutically acceptable polymorph, prodrug, salt, solvate, hydrate, or clathrate thereof, are encompassed by the invention. Individual dosage forms of the invention may be suitable for oral, mucosal (including rectal, nasal, or vaginal), parenteral (including subcutaneous, intramuscular, bolus injection, intraarterial, or intravenous), sublingual, transdermal, buccal, or topical administration.

Pharmaceutical compositions and dosage forms of the invention comprise stereomerically pure Compound A, or a pharmaceutically acceptable prodrug, metabolite, polymorph, salt, solvate, hydrate, or clathrate thereof. Pharmaceutical compositions and dosage forms of the invention typically also comprise one or more pharmaceutically acceptable excipients.

A particular pharmaceutical composition encompassed by this embodiment comprises stereomerically pure Compound A, or a pharmaceutically acceptable polymorph, prodrug, salt, solvate, hydrate, or clathrate thereof, and at least one additional therapeutic agent. Examples of additional therapeutic agents include, but are not limited to: anti-cancer drugs and anti-inflammation therapies including, but not limited to, those listed above in section 4.2.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disorder may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

Lactose-free compositions of the invention can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise compound A, or a pharmaceutically acceptable salt, solvate, clathrate, hydrate, polymorph or prodrug thereof lie within the range of from about 1 mg to about 1000 mg per day, given as a single once-a-day dose in the morning but preferably as divided doses throughout the day taken with food. More specifically, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response.

Oral Dosage Forms

Pharmaceutical compositions of the invention that are suitable for oral administration can be presented as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 16th and 18th eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a unit dosage form of compound A, or a pharmaceutically acceptable salt, solvate, hydrate, clathrate, polymorph or prodrug thereof, and a unit dosage form of a second active ingredient. Examples of second active ingredients include, but are not limited to, those listed in section 4.2 above.

Kits of the invention can further comprise devices that are used to administer the active ingredient(s). Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

EXAMPLES

Example 1

Synthesis of 2-[1-(3-Ethoxy-4-Methoxyphenyl)-2-Methylsulfonylethyl]-4-Acetylaminoisoindoline-1,3-Dione A stirred solution of 1-(3-ethoxy-4-methoxyphenyl)-2-methylsulfonylethylamine (1.0 g, 3.7 mmol) and 3-acetamidophthalic anhydride (751 mg, 3.66 mmol) in acetic acid (20 mL) was heated at reflux for 15 h. The solvent was removed in vacuo to yield an oil. Chromatography of the resulting oil yielded the product as a yellow solid (1.0 g, 59% yield): mp, 144° C.; $^1$H NMR (CDCl$_3$) δ1.47 (t, J=7.0 Hz, 3H, CH$_3$), 2.26 (s, 3H, CH$_3$), 2.88 (s, 3H, CH$_3$), 3.75 (dd, J=4.4, 14.3 Hz, 1H, CHH), 3.85 (s, 3H, CH3), 4.11 (q, J=7 Hz, 2H, CH2), 5.87 (dd, J=4.3, 10.5 Hz, 1H, NCH), 6.82-6.86 (m, 1H, Ar), 7.09-7.11 (m, 2H, Ar), 7.47 (d, J=7 Hz, 1H., Ar), 7.64 (t, J=8 Hz, 1H, Ar), 8.74 (d, J=8 Hz, 1H, Ar), 9.49 (br s, 1H, NH); $^{13}$C NMR (CDCl$_3$) 614.61, 24.85, 41.54, 48.44, 54.34, 55.85, 64.43, 111.37, 112.34, 115.04, 118.11, 120.21, 124.85, 129.17, 130.96, 136.01, 137.52, 148.54, 149.65, 167.38, 169.09, 169.40; Anal Calc'd. for $C_{22}H_{24}NO_7S$: C, 57.38; H, 5.25; N, 6.08. Found: C, 57.31; H, 5.34; N, 5.83.

Example 2

Synthesis of (+)2-[1-(3-Ethoxy-4-Methoxyphenyl)-2-Methylsulfonylethyl]-4-Acetylaminoisoindoline-1,3-Dione Preparation of 3-aminopthalic acid 10% Pd/C (2.5 g), 3-nitrophthalic acid (75.0 g, 355 mmol) and ethanol (1.5 L) were charged to a 2.5 L Parr hydrogenator, under a nitrogen atmosphere. Hydrogen was charged to the reaction vessel for up to 55 psi. The mixture was shaken for 13 hours, maintaining hydrogen pressure between 50 and 55 psi. Hydrogen was released and the mixture was purged with nitrogen 3 times. The suspension was filtered through a celite bed and rinsed with methanol. The filtrate was concentrated in vacuo. The resulting solid was reslurried in ether and isolated by vacuum filtration. The solid was dried in vacuo to a constant weight, affording 54 g (84% yield) of 3-aminopthalic acid as a yellow product. $^1$H-NMR (DMSO-d6) δ: 3.17 (s, 2H), 6.67 (d, 1H), 6.82 (d, 1H), 7.17 (t, 1H), 8-10 (brs, 2H). $^{13}$C-NMR (DMSO-d6) δ: 112.00, 115.32, 118.20, 131.28, 135.86, 148.82, 169.15, 170.09.

Preparation of 3-acetamidophthalic anhydride

A 1 L 3-necked round bottom flask was equipped with a mechanical stirrer, thermometer, and condenser and charged with 3-aminophthalic acid (108 g, 596 mmol) and acetic anhydride (550 mL). The reaction mixture was heated to reflux for 3 hours and cooled to ambient temperature and further to 0-5° C. for another 1 hour. The crystalline solid was collected by vacuum filtration and washed with ether. The solid product was dried in vacuo at ambient temperature to a constant weight, giving 75 g (61% yield) of 3-acetamidopthalic anhydride as a white product. $^1$H-NMR (CDCl$_3$) δ: 2.21 (s, 3H), 7.76 (d, 1H), 7.94 (t, 1H), 8.42 (d, 1H), 9.84 (s, 1H).

Resolution of 2-(3-ethoxy-4-methoxyphenyl)-1-(methylsulphonyl)-eth-2-ylamine

A 3 L 3-necked round bottom flask was equipped with a mechanical stirrer, thermometer, and condenser and charged with 2-(3-ethoxy-4-methoxyphenyl)-1-(methylsulphonyl)-eth-2-ylamine (137.0 g, 500 mmol), N-acetyl-L-leucine (52 g, 300 mmol), and methanol (1.0 L). The stirred slurry was heated to reflux for 1 hour. The stirred mixture was allowed to cool to ambient temperature and stirring was continued for another 3 hours at ambient temperature. The slurry was filtered and washed with methanol (250 mL). The solid was air-dried and then dried in vacuo at ambient temperature to a constant weight, giving 109.5 g (98% yield) of the crude product (85.8% ee). The crude solid (55.0 g) and methanol (440 mL) were brought to reflux for 1 hour, cooled to room temperature and stirred for an additional 3 hours at ambient temperature. The slurry was filtered and the filter cake was washed with methanol (200 mL). The solid was air-dried and then dried in vacuo at 30° C. to a constant weight, yielding 49.6 g (90% recovery) of (S)-2-(3-ethoxy-4-methoxyphenyl)-1-(methylsulphonyl)-eth-2-ylamine-N-acetyl-L-leucine salt (98.4% ee). Chiral HPLC (1/99 EtOH/20 mM KH$_2$PO$_4$@pH 7.0, Ultron Chiral ES-OVS from Agilent Technologies, 150 mm×4.6 mm, 0.5 mL/min., @240 nm): 18.4 min (S-isomer, 99.2%), 25.5 min (R-isomer, 0.8%).

Preparation of Compound A

A 500 mL 3-necked round bottom flask was equipped with a mechanical stirrer, thermometer, and condenser. The reaction vessel was charged with (S)-2-(3-ethoxy-4-methoxyphenyl)-1-(methylsulphonyl)-eth-2-yl amine N-acetyl-L-leucine salt (25 g, 56 mmol, 98% ee), 3-acetamidophthalic anhydride (12.1 g 58.8 mmol), and glacial acetic acid (250 mL). The mixture was refluxed over night and then cooled to <50° C. The solvent was removed in vacuo, and the residue was dissolved in ethyl acetate. The resulting solution was washed with water (250 mL×2), saturated aqueous NaHCO$_3$ (250 mL×2), brine (250 mL×2), and dried over sodium sulphate. The solvent was evaporated in vacuo, and the residue recrystallized from a binary solvent containing ethanol (150 mL) and acetone (75 mL). The solid was isolated by vacuum filtration and washed with ethanol (100 mL×2). The product was dried in vacuo at 60° C. to a constant weight, affording 19.4 g (75% yield) of S-{2-[1-(3-ethoxy-4-methoxyphenyl)-2-methylsulfonylethyl]-4-aminoisoindoline-1,3-dione with 98% ee. Chiral HPLC (15/85 EtOH/20 mM KH$_2$PO$_4$ @pH 3.5, Ultron Chiral ES-OVS from Agilent Technology, 150 mm×4.6 mm, 0.4 mL/min., @240 nm): 25.4 min (S-isomer, 98.7%), 29.5 min (R-isomer, 1.2%). $^1$H-NMR (CDCl$_3$) δ: 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H). $^{13}$C-NMR (DMSO-d6) δ: 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48.

Example 3

TNF-α Inhibition

Human Whole Blood LPS-induced TNF-α Assay

The ability of compounds to inhibit LPS-induced TNF-α production by human whole blood was measured essentially as described below for the LPS-induced TNF-α assay in human PBMC, except that freshly drawn whole blood was used instead of PBMC. (George Muller, et al. 1999, *Bioorganic & Medicinal Chemistry Letters* 9; 1625-1630.) Human whole blood LPS-induced TNF-α IC$_{50}$—294 nM Mouse LPS-induced Serum TNF-α Inhibition Compounds were tested in this animal model according to previously described methods (Corral et al. 1996, *Mol. Med.* 2:506-515). Mouse LPS-induced serum TNF-α inhibition (ED$_{50}$, mg/kg, p.o.)=0.05.

LPS-induced TNF-α Production

Lipopolysaccharide (LPS) is an endotoxin produced by gram-negative bacteria such as *E. coli* which induces production of many pro-inflammatory cytokines, including TNF-α. In peripheral blood mononuclear cells (PBMC), the TNF-α produced in response to LPS is derived from monocytes, which comprise approximately 5-20% of the total PBMC. Compounds were tested for the ability to inhibit LPS-induced TNF-α production from human PBMC as previously described (Muller et al. 1996, *J. Med. Chem.* 39:3238). PBMC from normal donors were obtained by Ficoll Hypaque (Pharmacia, Piscataway, N.J., USA) density centrifugation. Cells were cultured in RPMI (Life Technologies, Grand Island, N.Y., USA) supplemented with 10% AB±human serum (Gemini Bio-products, Woodland, Calif., USA), 2 mM L-glutamine, 100 U/ml penicillin, and 100 μg/ml streptomycin (Life Technologies).

PBMC ($2\times10^5$ cells) were plated in 96-well flat-bottom Costar tissue culture plates (Corning, N.Y., USA) in triplicate. Cells were stimulated with LPS (Sigma, St. Louis, Mo., USA) at 100 ng/ml in the absence or presence of compounds. Compounds (Celgene Corp., Warren, N.J., USA) were dissolved in DMSO (Sigma) and further dilutions were done in culture medium immediately before use. The final DMSO concentration in all samples was 0.25%. Compounds were added to cells 1 hour before LPS stimulation. Cells were incubated for 18-20 hours at 37° C. in 5% $CO_2$ and supernatants were then collected, diluted with culture medium and assayed for TNF-α levels by ELISA (Endogen, Boston, Mass., USA). LPS-induced TNF-α $IC_{50}$=77 nM.

IL-1β-induced TNF-α Production

During the course of inflammatory diseases, TNF-α production is often stimulated by the cytokine 1L-1β, rather than by bacterially derived LPS. Compounds were tested for the ability to inhibit IL-1β-induced TNF-α production from human PBMC as described above for LPS-induced TNF-α production, except that the PBMC were isolated from source leukocyte units (Sera-Tec Biologicals, North Brunswick, N.J., USA) by centrifugation on Ficoll-Paque Plus (Amersham Pharmacia, Piscataway, N.J., USA), plated in 96-well tissue culture plates at $3\times10^5$ cells/well in RPMI-1640 medium (BioWhittaker, Walkersville, Md., USA) containing 10% heat-inactivated fetal bovine serum (Hyclone), 2 mM L-glutamine, 100 U/ml penicillin, and 100 mg/ml streptomycin (complete medium), pretreated with compounds at 10, 2, 0.4, 0.08, 0.016, 0.0032, 0.00064, and 0 μM in duplicate at a final DMSO concentration of 0.1% at 37° C. in a humidified incubator at 5% $CO_2$ for 1 hour, then stimulated with 50 ng/ml recombinant human IL-1β (Endogen) for 18 hours. IL-β-induced TNF-α $IC_{50}$=83 nM.

Example 4

PDE Selectivity

PDE1, 2, 3, 5, and 6 Enzyme Assays

The specificity of compounds for PDE4 was assessed by testing at a single concentration (10 μM) against bovine PDE1, human PDE2, PDE3, and PDE5 from human platelets (Hidaka and Asano 1976, *Biochem. Biophys. Acta* 429:485, and Nicholsen et al. 1991, *Trends Pharmaco. Sci.* 12:19), and PDE6 from bovine retinal rod outer segments (Baehr et al. 1979, J. Biol. Chem. 254:11669, and Gillespie et al. 1989, *Mol. Pharm.* 36:773). Results are listed in Table 1.

PDE7 Enzyme Assay

PDE7 is a cAMP-selective PDE expressed mainly in T cells and in skeletal muscle. T cell-derived cytokines such as IL-2 and IFN-γ are potentially regulatable via PDE7 inhibition. PDE7 was purified from Hut78 human T cells by anion exchange chromatography as previously described (Bloom and Beavo 1996, *Proc. Natl. Acad. Sci. USA* 93:14188-14192). Compounds were tested against the PDE7 preparation in the presence of 10 nM cAMP as described for PDE4 in Table 1 below.

TABLE 1

|  | Racemic Compound | Compound A | Compound B* |
|---|---|---|---|
| PDE Inhibition |  |  |  |
| PDE4 $IC_{50}$ (from U937 cells) (nM) | 81.8 | 73.5 | 611 |
| PDE1 (% inhib at 10 μM) | 9% | 23% | 27% |
| PDE2 (% inhib at 10 μM) | 19% | 6% | 10% |
| PDE3 (% inhib at 10 μM) | 21% | 20% | 31% |
| PDE5 (% inhib at 10 μM) | 3% | 3% | −9% |
| PDE6 (% inhib at 10 μM) | ND | −6% | 10% |
| PDE7 $IC_{50}$ (nM) | 22110 | 20500 | ND |
| PDE Specificity Ratios from above data (*fold) |  |  |  |
| PDE4/PDE1 | >2700 | >500 | >50 |
| PDE4/PDE2 | >800 | >10000 | >260 |
| PDE4/PDE3 | >670 | >1200 | >45 |
| PDE4/PDE5 | >12000 | >30000 | >39000 |
| PDE4/PDE6 | ND | >40000 | >250 |
| PDE7 $IC_{50}$/PDE4 $IC_{50}$ | 270 | 279 | ND |

*Compound B is the opposite enantiomer of Compound A.

Example 5

PDE4 Inhibition

PDE4 (U937 Cell-derived) Enzyme Assay

PDE4 enzyme was purified from U937 human monocytic cells by gel filtration chromatography as previously described (Muller et al. 1998, *Bioorg. & Med Chem Lett* 8:2669-2674). Phosphodiesterase reactions were carried out in 50 mM Tris HCl pH 7.5, 5 mM $MgCl_2$, 1 μM cAMP, 10 nM [$^3$H]-cAMP for 30 min at 30° C., terminated by boiling, treated with 1 mg/ml snake venom, and separated using AG-IXS ion exchange resin (BioRad) as described (Muller et al. 1998, *Bioorg. & Med Chem Lett* 8:2669-2674). Reactions consumed less than 15% of available substrate. Results are listed in Table 1.

Example 6

Human T Cell Assays

SEB-induced IL-2 and IFN-γ Production

Staphylococcal Enterotoxin B (SEB) is a superantigen derived from gram-positive bacteria *Staphylococcus aureus*. SEB provides a convenient physiological stimulus specific for T cells expressing particular T cell receptor Vβ chains. Human PBMC (consisting of approximately 50% T cells) were isolated from source leukocyte units as described above and plated in 96-well tissue culture plates at $3\times10^5$ cells/well in complete medium, pretreated with compounds at 10, 2, 0.4, 0.08, 0.016, 0.0032, 0.00064, and 0 μM in duplicate at a final DMSO concentration of 0.1% at 37° C. in a humidified incubator at 5% $CO_2$ for 1 hour, then stimulated with 100 ng/ml SEB (Sigma Chemical Co., St. Louis, Mo., USA) for 18 hours. IL-2 and IFN-γ levels were measured by ELISA (R&D Systems, Minneapolis, Minn., USA). IL-2 $IC_{50}$=291 nM. IFN-γ $IC_{50}$=46 nM.

Example 6 cAMP Elevation Assays $PGE_2$-induced cAMP Elevation

Prostaglandin $E_2$ ($PGE_2$) binds to prostanoid receptors on monocytes, T cells and other leukocytes and consequently elevates intracellular cAMP levels, resulting in inhibition of cellular responses. The combination of $PGE_2$ and a PDE4 inhibitor synergistically elevates cAMP levels in these cell types, and the elevation of cAMP in PBMC caused by PDE4 inhibitors in the presence of $PGE_2$ is proportional to the inhibitory activity of that PDE4 inhibitor. Intracellular cAMP was measured in human PBMC as follows. PBMC were isolated as described above and plated in 96-well plates at $1\times10^6$ cells per well in RPMI-1640. The cells were pretreated with compounds at 100, 10, 1, 0.1, 0.01, and 0 µM in a final concentration of 2% DMSO in duplicate at 37° C. in a humidified incubator at 5% $CO_2$ for one hour. The cells were then stimulated with $PGE_2$ (10 µM) (Sigma) for 1 h. The cells were lysed with HCl, 0.1 N final concentration to inhibit phosphodiesterase activity and the plates were frozen at –20° C. The cAMP produced was measured using cAMP (low pH) Immunoassay kit (R&D Systems). PBMC cAMP EC, for racemate is 3.09 µM. PBMC cAMP EC, for Compound A is 1.58 µM.

Elevation of cAMP in human neutrophils was measured as follows. PBMC were removed from source leukocytes (Sera-Tec Biologicals) by centrifugation on Ficoll—Paque Plus (Amersham Pharmacia). The resulting erythrocyte/polymorphonuclear cell (PMN) pellet was resuspended in Hank's Balanced Salt Solution (BioWhittaker) and mixed with an equal volume of 3% Dextran T-500 (Amersham Pharmacia) in 0.9% saline. Erythrocytes were allowed to sediment for 20 minutes, and the PMN were removed and centrifuged at 120 rpm for 8 minutes at 4° C. The remaining erythrocytes were lysed in cold 0.2% saline for 30 seconds, and the cells restored to isotonicity by the addition of an equal volume of 1.6% saline. The PMN were centrifuged at 1200 rpm for 8 minutes at 4° C., then resuspended in RPMI-1640 and assayed for cAMP elevation as described for PBMC above. PMN were found to be approximately 74% $CD18/CD11b^+$, 71% $CD16^+$ $CD9^+$ neutrophils by flow cytometzy on a FACSCalibur (Becton Dickinson, San Jose, Calif., USA). Results are shown in Table 2.

fMLF-Induced LTB4 Production

N-formyl-methionine-leucine-phenylalanine (fMLF) is a bacterially derived peptide that activates neutrophils to rapidly degranulate, migrate, adhere to endothelial cells, and release leukotriene LTB4, a product of arachidonic acid metabolism and itself a neutrophil chemoattractant. Compounds were tested for the ability to block fMLF-induced neutrophil LTB4 production as previously described (Hatzelmann and Schudt 2001, *J. Pharm. Exp. Ther.* 297:267-279), with the following modifications. Neutrophils were isolated as described above and resuspended in phosphate-buffered saline without calcium or magnesium (BioWhittaker) containing 10 mM HEPES pH7.2 and plated in 96-well tissue culture plates at a concentration of $1.7\times10^6$ cells/well. Cells were treated with 50 µM thimerosal (Sigma)/1 mM $CaCl_2$/1 mM $MgCl_2$ for 15 minutes at 37° C. 5% $CO_2$, then treated with compounds at 1000, 200, 40, 8, 1.6, 0.32, 0.064, and 0 nM in a final DMSO concentration of 0.01% in duplicate for 10 minutes. Neutrophils were stimulated with 1 µM fMLF for 30 minutes, then lysed by the addition of methanol (20% final concentration) and frozen in a dry ice/isopropanol bath for 10 minutes. Lysates were stored at –70° C. until the LTB4 content was measured by competitive LTB4 ELISA (R&D Systems). Results are shown in Table 2.

Zymosan-induced IL-8 Production

Zymosan A, or the heat-killed yeast *Saccharomyces cerevisiae*, binds to the adhesion molecule Mac-1 on the neutrophil surface and triggers phagocytosis, cell activation and IL-8 production. Zymosan-induced IL-8 production was measured as previously described (Au et al. 1998, *Brit. J. Pharm.* 123:1260-1266) with the following modifications. Human neutrophils were purified as described above, plated in 96-well tissue culture plates at $3\times10^5$ cells/well in complete medium, treated with compounds at 10, 2, 0.4, 0.08, 0.016, 0.0032, 0.00064, and 0 µM in duplicate in a final DMSO concentration of 0.1% for 1 hour at 37° C. 5% $CO_2$. Neutrophils were then stimulated with unopsonized, boiled Zymosan A (Sigma) at $2.5\times10^5$ particles/well for 18 hours. Supernatants were harvested and tested for IL-8 by ELISA (R&D Systems). Results are shown in Table 2.

fMLF-induced CD18/CD11b Expression

CD18/CD11b (Mac-1) expression on neutrophils was measured as previously described (Derian et al. 1995, *J. Immunol.*: 154:308-3 17) with the following modifications. Neutrophils were isolated as described above, then resuspended in complete medium at $1\times10^6$ cells/ml, pretreated with compounds at 10, 1, 0.1, 0.01, and 0 µM in duplicate at a final DMSO concentration of 0.1% for 10 minutes at 37° C. 5% $CO_2$. Cells were then stimulated with 30 nM fMLF for 30 minutes and then chilled to 4° C. Cells were treated with rabbit IgG (Jackson ImmunoResearch Labs, West Grove, Pa., USA) (10 µg/$1\times10^6$ cells) to block Fc receptors, stained with CD18-FITC and CD11b-PE (Becton Dickinson), and analyzed by flow cytometry on a FACSCalibur. CD18/CD11b expression (mean fluorescence) in the absence of stimulation was subtracted from all samples to obtain inhibition curves and calculate $IC_{50}$s. Results are shown in Table 2.

fMLF-induced Adhesion to HUVEC

Human umbilical vein endothelial cells (HUVEC) were used as a substrate for neutrophil adhesion as previously described (Derian et al. 1995, *J. Immunol.*: 154:308-317) with the following modifications. HUVEC cells were obtained from Anthrogenesis (Cedar Knolls, N.J., USA), and neutrophils were not treated with cytochalasin B. Cells were treated with compounds at 10, 1, 0.1, 0.01, 0.001, and 0 µM in a final DMSO concentration of 0.1% in duplicate for 10 minutes, stimulated with 500 nM fMLF for 30 minutes, and washed twice with PBS before measuring fluorescence on an FLX800 plate reader (Bio-Tek Instruments, Winooski, Vt., USA). Results are shown in Table 2.

TABLE 2

| Human Neutrophil Assays (all values in nM) | Racemic Compound | Compound A |
|---|---|---|
| $PGE_2$-induced cAMP $EC_{50}$ | 12589 | 4570 |
| fMLF-induced LTB4 $IC_{50}$ | 20.1 | 2.48 |
| Zymosan-induced IL-8 $IC_{50}$ | ND | 94 |
| fMLF-induced CD18 expression $IC_{50}$ | ND | 390 |
| fMLF-induced CD11b expression $IC_{50}$ | ND | 74 |
| fMLF-induced adhesion to HUVEC $IC_{50}$ | ND | 150 |

Example 8

Aqueous Solubility

Equilibrium solubilities were measured in pH 7.4 aqueous buffer. The pH 7.4 buffer was prepared by adjusting the pH of a 0.07 M NaH$_2$PO$_4$ solution to 7.4 with 10 N NaOH. The ionic strength of the solution was 0.15. At least 1 mg of powder was combined with 1 ml of buffer to make >1 mg/ml mixture. These samples were shaken for >2 hours and left to stand overnight at room temperature. The samples were then filtered through a 0.45-μm Nylon syringe filter that was first saturated with the sample. The filtrate was sampled twice, consecutively. The filtrate was assayed by HPLC against standards prepared in 50% methanol. Compound A has 3.5-fold greater aqueous solubility than the racemic mixture. Measured solubility Compound A=0.012 mg/mL; racemic mixture=0.0034 mg/mL.

Example 8

LPS-induced Lung Neutrophilia Ferret Model

The conscious ferret model has been used to investigate anti-inflammatory, emetic and behavioral effects of PDE4 inhibitors when administered by the oral (p.o.) route. From these experiments, a therapeutic index (TI) for each PDE4 inhibitor may be determined. The TI has been calculated by dividing the threshold dose for causing emetic episodes and behavioral changes by the anti-inflammatory dose (dose that causes 50% inhibition of the LPS-induced neutrophilia).

Animal Husbandry

Male ferrets (Mustela Pulorius Euro, weighing 1-2 kg). Ferrets were supplied either by Bury Green Farm or Misay Consultancy. Following transport, the animals were allowed to acclimatize in the holding rooms for a period of not less than 7 days. The Diet comprised SDS diet C pelleted food given ad lib with Whiskers cat food given 3 times per week. Water was pasteurized animal grade drinking water and was changed daily.

Dosing with PDE4 Inhibitor

PDE4 inhibitors were administered orally (p.o.), at doses initially of 1-10 mg/kg, but subsequently up to 30 mg/kg in order to establish whether the TI was 10 or higher, and/or at lower doses to establish the minimum dose to cause 50% inhibition of neutrophilia. Ferrets were fasted overnight but allowed free access to water. The animals were orally dosed with vehicle or PDE4 inhibitor using a 15 cm dosing needle that was passed down the back of the throat into the oesophagus. After dosing, the animals were returned to holding cages fitted with Perspex doors to allow observation, and given free access to water. After dosing, the animals were constantly observed and any emesis or behavioural changes were recorded. The animals were allowed access to food 60-90 minutes after p.o. dosing Exposure to LPS Thirty minutes after p.o. dosing with compound or vehicle control, the ferrets were placed into sealed Perspex containers and exposed to an aerosol of LPS (100 μg/ml) for 10 minutes. Aerosols of LPS were generated by a nebulizer (DeVilbiss, USA) and this was directed into the Perspex exposure chamber. Following a 10 minute exposure period, the animals were returned to the holding cages and allowed free access to water, and at a later stage, food. Observation continued for a period of at least 2.5 hours post p.o. dosing and emetic episodes and behavioral changes were recorded.

Bronchoalveolar Lavage

Six hours after LPS exposure the animals were killed by overdose of sodium pentobarbitone administered intraperitoneally. The trachea was then cannulated with polypropylene tubing and the lungs lavaged twice with 20 ml heparinized (10 units/ml) phosphate buffered saline (PBS).

Blood Sampling/Tissue Removal

A terminal blood sample (10 ml) was removed by transthoracic cardiac puncture. The blood was spun at 2500 rpm for 15 minutes and the plasma removed and stored at −20° C. The brain also removed and frozen at −20° C. for analysis of compound content.

Cell Counts

The bronchoalveolar lavage (BAL) samples were centrifuged at 1500 rpm for 5 minutes. The supernatant was removed and the resulting cell pellet re-suspended in 1 ml PBS. A cell smear of the re-suspended fluid was prepared and stained with Leishmans stain to allow differential cell counting. A total cell count was made using the remaining re-suspended sample. From this, the total number of neutrophils in the BAL was determined.

Parameters Measured:

1. % Inhibition of LPS-induced pulmonary neutrophilia.
2. Emetic episodes—the number of vomits and retches were counted.
3. Behavioral changes—the following behavioral effects were noted: salivation, panting, mouth clawing, flattened posture, ataxia, arched back and backward walking. Any behavioral changes were semi-quantified by applying a severity rating (mild, moderate or severe).
4. The TI was calculated as the highest dose found to not cause emetic episodes divided by the lowest dose found to inhibit pulmonary neutrophilia by 50% or more.

The effect of Compound A on LPS-induced neutrophilia in the lungs of conscious ferrets is demonstrated in FIG. 1.

Emesis and Behavioral Changes

Following p.o. dosing of the PDE4, the ferrets were observed for at least 2 hours and emetic episodes (vomits and retches) and behavioral changes were recorded.

No emetic episodes (retching or vomiting) were observed in the ferrets pre-treated p.o. with the relevant vehicle (acetone/cremophor/distilled water). In a small proportion of the control-treated animals (7/22), mild behavioral changes (lip licking and backward walking) were seen.

Compound A (0.1-3 mg/kg, p.o.), caused no emetic episodes (retching and vomiting). Some behavioral changes (flattened posture, lip licking and backward walking) were observed and classified as mild. At 10 mg/kg in 2/6 ferrets, some retching but no frank emesis was observed along with salivation and behavioral changes (scored as mild or moderate). At the highest dose tested (30 mg/kg) moderate to marked emesis was observed in 3/4 animals along with pronounced behavioral changes. These data are summarized in Table II.

TABLE III

Conscious ferret: Emetic episodes and behavioural changes following oral administration of Compound A.

| Treatment/ dose (mg/kg) | Vomits | Retches | Salivation | Panting | Mouth clawing | Flattened posture | Ataxia | Lip licking | Backward walking |
|---|---|---|---|---|---|---|---|---|---|
| Vehicle (acetone/cremophor/ dist. H2O) | None | None | None | None | None | None | None | Mild (6/22) | Mild (7/22) |

TABLE III-continued

Conscious ferret: Emetic episodes and behavioural changes following oral administration of Compound A.

| Treatment/ dose (mg/kg) | Vomits | Retches | Salivation | Panting | Mouth clawing | Flattened posture | Ataxia | Lip licking | Backward walking |
|---|---|---|---|---|---|---|---|---|---|
| Compound A (0.1 mg/kg) | None | None | None | None | None | Mild (2/5) | None | Mild (4/5) | Mild (3/5) |
| Compound A (0.3 mg/kg) | None | None | None | None | None | Mild (2/6) | None | Mild (3/6) | Mild (4/6) |
| Compound A (1.0 mg/kg) | None | None | None | None | None | Mild (2/6) | None | Mild (6/6) | Mild (4/6) |
| Compound A (3.0 mg/kg) | None | None | None | None | Mild (1/8) | Marked (7/8) | None | Mild (2/8) | Moderate (5/8) |
| Compound A (10 mg/kg) | None | Mild (2/6) | Mild (1/6) | None | Mild (1/6) | Marked (6/6) | None | Moderate (5/6) | Marked (6/6) |
| Compound A (30 mg/kg) | Moderate (3/4) | Marked (3/4) | Moderate (3/4) | Mild (1/4) | Marked (4/4) | Marked (4/4) | Mild (3/4) | Moderate (4/4) | Mild (2/4) |

Animals were observed for up to 3 hours following dosing. Numbers in parentheses refer to the number of animals that responded The numbers of animals in each group range from 4-22.

Therapeutic Index Calculation

From these experiments, a therapeutic index (TI) was determined for each compound by dividing the threshold dose for inducing emetic episodes by the $ED_{50}$ value for inhibiting the pulmonary neutrophilia. The TI calculation is summarized in Table IV. Compound A had a TI of 12, causing no emetic episodes at an anti-inflammatory dose of 1 mg/kg.

TABLE IV

Summary of the effective doses ($ED_{50}$) for inhibition of LPS-induced pulmonary neutrophilia and induction of emesis and the therapeutic index derived from these values.

| Compound | Inhibition of LPS-induced neutrophilia ($ED_{50}$ mg/kg) | Threshold emetic dose (mg/kg) | Therapeutic index |
|---|---|---|---|
| Compound A | 0.8 | 10 | 12 |

Example 9

200 mg Dosage Capsule

Table V illustrates a batch formulation and single dosage formulation for a 200 mg Compound A single dose unit, i.e., about 40 percent by weight, in a size #0 capsule.

TABLE V

Formulation for 200 mg capsule

| Material | Percent By Weight | Quantity (mg/tablet) | Quantity (kg/batch) |
|---|---|---|---|
| Compound A | 40.0% | 200 mg | 16.80 kg |
| Pregelatinized Corn Starch, NF5 | 9.5% | 297.5 mg | 24.99 kg |
| Magnesium Stearate | 0.5% | 2.5 mg | 0.21 kg |
| Total | 100.0% | 500 mg | 42.00 kg |

The pregelatinized corn starch (SPRESS B-820) and Compound A components are passed through a 710 μm screen and then are loaded into a Diffusion Mixer with a baffle insert and blended for 15 minutes. The magnesium stearate is passed through a 210 μm screen and is added to the Diffusion Mixer. The blend is then encapsulated in a size #0 capsule, 500 mg per capsule (8400 capsule batch size) using a Dosator type capsule filling machine.

Example 10

100 mg Oral Dosage Form

Table VI illustrates a batch formulation and a single dose unit formulation containing 100 mg of Compound A.

TABLE VI

Formulation for 100 mg tablet

| Material | Percent by Weight | Quantity (mg/tablet) | Quantity (kg/batch) |
|---|---|---|---|
| Compound A | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and Compound A components are passed through a #30 mesh screen (about 430μ to about 655μ). The Pluronic F-68® (manufactured by JRH Biosciences, Inc. of Lenexa, Kans.) surfactant is passed through a #20 mesh screen (about 457μ to about 1041μ). The Pluronic F-68® surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The thalidomide is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 250 mg per tablet (200,000 tablet batch size).

Example 11

Aerosol Dosage Form

A concentrate is prepared by combining Compound A, and a 12.6 kg portion of the trichloromonofluoromethane in a sealed stainless steel vessel equipped with a high shear mixer. Mixing is carried out for about 20 minutes. The bulk suspension is then prepared in the sealed vessel by combining the concentrate with the balance of the propellants in a bulk product tank that is temperature controlled to 21° to 27° C. and pressure controlled to 2.8 to 4.0 BAR. 17 ml aerosol containers which have a metered valve which is designed to provide 100 inhalations of the composition of the invention. Each container is provided with the following:

| | |
|---|---|
| Compound A | 0.0120 g |
| trichloromonofluoromethane | 1.6939 g |
| dichlorodifluoromethane | 3.7175 g |
| dichlorotetrafluoroethane | 1.5766 g |
| total | 7.0000 g |

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A method of treating a disease or disorder selected from Crohn's Disease or ulcerative colitis, the method comprising administering to a patient having a Crohn's Disease or ulcerative colitis a therapeutically effective amount of a compound which is stereomerically pure (+)-2-[1-(3-ethoxy-4-methoxyphenyl)-2-methylsulfonylethyl]-4-acetylaminoisoindoline-1,3-dione, or a pharmaceutically acceptable salt thereof.

2. The method of claim 1 further comprising administering to the patient a therapeutically effective amount of an antihistamine, anti-inflammatory drug, non-steroid anti-inflammatory drug, or steroid.

3. The method of claim 1 wherein the compound is administered parenterally, transdermally, mucosally, nasally, buccally, sublingually, or orally.

4. The method of claim 3 wherein the compound is administered orally.

5. The method of claim 4 wherein the compound is administered orally in a tablet or capsule form.

6. The method of claim 1 wherein the therapeutically effective amount is from about 1 mg to about 1000 mg per day.

7. The method of claim 6 wherein the therapeutically effective amount is from about 5 mg to about 500 mg per day.

8. The method of claim 7 wherein the therapeutically effective amount is from about 10 mg to about 200 mg per day.

9. The method of claim 1, wherein the disease or disorder is Crohn's Disease.

10. The method of claim 1, wherein the disease or disorder is ulcerative colitis.

11. The method of claim 4, wherein the compound is administered twice daily in equally divided doses.

12. The method of claim 4, wherein the stereomerically pure compound comprises greater than about 90% by weight of (+) isomer based on the total weight percent of the compound.

13. The method of claim 4, wherein the stereomerically pure compound comprises greater than about 95% by weight of (+) isomer based on the total weight percent of the compound.

14. The method of claim 4, wherein the stereomerically pure compound comprises greater than about 97% by weight of (+) isomer based on the total weight percent of the compound.

15. The method of claim 5, wherein the capsule contains about 10 mg of the compound.

16. The method of claim 5, wherein the capsule contains about 20 mg of the compound.

17. The method of claim 5, wherein the capsule contains about 25 mg of the compound.

18. The method of claim 5, wherein the capsule contains about 50 mg of the compound.

19. The method of claim 5, wherein the tablet contains about 10 mg of the compound.

20. The method of claim 5, wherein the tablet contains about 20 mg of the compound.

21. The method of claim 5, wherein the tablet contains about 25 mg of the compound.

22. The method of claim 5, wherein the tablet contains about 50 mg of the compound.

23. A method of treating Crohn's Disease, which comprises orally administering to a patient having Crohn's Disease about 10 mg to about 100 mg of a compound which is stereomerically pure (+)-2-[1-(3-ethoxy-4-methoxyphenyl)-2-methylsulfonylethyl]-4-acetylaminoisoindoline-1,3-dione comprising greater than about 97% by weight of (+) isomer, wherein the compound is administered in the form of a tablet or capsule twice daily in equally divided doses.

24. A method of treating ulcerative colitis, which comprises orally administering to a patient having ulcerative colitis about 10 mg to about 100 mg of a compound which is stereomerically pure (+)-2-[1-(3-ethoxy-4-methoxyphenyl)-2-methylsulfonylethyl]-4-acetylaminoisoindoline-1,3-dione comprising greater than about 97% by weight of (+) isomer, wherein the compound is administered in the form of a tablet or capsule twice daily in equally divided doses.

* * * * *